United States Patent [19]

Reiter

[11] Patent Number: 4,560,690
[45] Date of Patent: Dec. 24, 1985

[54] 2-(N-SUBSTITUTED GUANIDINO)-4-HETERO-ARYLTHIAZOLE ANTIULCER AGENTS

[75] Inventor: Lawrence A. Reiter, Gales Ferry, Conn.

[73] Assignee: Pfizer Inc., New York, N.Y.

[21] Appl. No.: 605,510

[22] Filed: Apr. 30, 1984

[51] Int. Cl.$^4$ .................. C07D 417/04; C07D 417/14; A61K 31/425

[52] U.S. Cl. .................................... 514/256; 514/341; 514/342; 514/370; 544/333; 546/276; 546/278; 546/280; 548/190; 548/193; 548/198; 548/266; 548/262

[58] Field of Search ............... 548/190, 193, 198; 544/333; 546/276, 278, 280; 514/370, 341, 342, 256

[56] References Cited

U.S. PATENT DOCUMENTS

| | | | |
|---|---|---|---|
| 2,455,807 | 12/1948 | Redmon et al. | 260/551 |
| 4,098,898 | 7/1978 | Durant | 424/273 |
| 4,283,408 | 8/1981 | Hirata | 424/270 |
| 4,362,728 | 12/1982 | Yellin | 424/249 |
| 4,374,843 | 2/1983 | LaMattina et al. | 424/270 |
| 4,435,396 | 3/1984 | LaMattina et al. | 424/248.51 |

OTHER PUBLICATIONS

F. H. S. Curd et al., J. Chem. Soc., 1630, (1948).

Primary Examiner—Robert Gerstl
Attorney, Agent, or Firm—Charles J. Knuth; Albert E. Frost; Paul D. Thomas

[57] ABSTRACT 2,4-Disubstituted thiazole compounds of the formula

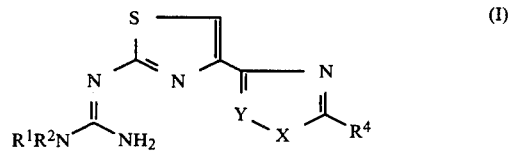

or a pharmaceutically acceptable acid addition salt thereof wherein X is NH and Y is CH or N, or
X is S and Y is CH;
$R^1$ is certain straight or branched chain alkyl groups, $(R^3)_2C_6H_3$, or $(R^3)_2Ar(CH_2)_n$ where n is an integer from 1 to 4, $R^3$ is H or certain substituent groups and Ar is phenylene, naphthalene or the residue of certain heteroaromatic groups;
$R^2$ is H or $(C_1-C_4)$alkyl; or
$R^1$ and $R^2$ taken together with the nitrogen atom to which they are attached form certain heterocyclic groups; and
$R^4$ is H, $(C_1-C_5)$alkyl, $NH_2$ or $CH_2OH$; a method for their use in treatment of gastric ulcers in mammals and pharmaceutical compositions containing said compounds.

27 Claims, No Drawings

2-(N-SUBSTITUTED GUANIDINO)-4-HETERO-ARYLTHIAZOLE ANTIULCER AGENTS

BACKGROUND OF THE INVENTION

The present invention relates to novel 2-(N-substitutedguanidino)-4-heteroarylthiazoles wherein said guanidino group is mono-, di- or trisubstituted and said heteroaryl substituent is an imidazol-4-yl, thiazol-4-yl or 1,2,4-triazol-5-yl group. These compounds have activity as antisecretory agents, histamine-$H_2$ receptor antagonists and/or as inhibitors of ethanol-induced gastric ulceration, useful in inhibiting (i.e. preventing and treating) peptic ulcers in mammals, including humans.

Chronic gastric and duodenal ulcers, together known as peptic ulcers, are a common ailment for which a variety of treatments, including dietary measures, drug therapy and surgery, may be employed, depending on the severity of the condition. Particularly valuable therapeutic agents useful for the treatment of gastric hyperacidity and peptic ulcers are the histamine-$H_2$ receptor antagonists, which act to block the action of the physiologically active compound histamine at the $H_2$-receptor sites in the animal body and to thereby inhibit the secretion of gastric acid. The determination that many of the present compounds will also inhibit ethanol-induced ulcers in rats, further reflects the clinical value of the present compounds in the inhibition of gastric ulcers.

LaMattina and Lipinski in U.S. Pat. No. 4,374,843 issued Feb. 22, 1983 have disclosed a class of 2-guanidino-4-heteroarylthiazole compounds useful for treatment of gastric hyperacidity and peptic ulcers, said compounds having the formula

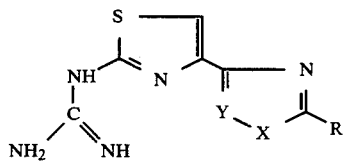

(XII)

wherein X is S or NH; Y is CH, CCH$_3$ or N and R is H, CH$_2$OH, (C$_1$–C$_6$)alkyl, Ph(CH$_2$)$_x$ or NH$_2$ which may be optionally alkylated or acylated; Ph is phenyl or monosubstituted phenyl and x is an integer from 2 to 4.

In U.S. Pat. No. 4,435,396 issued Mar. 6, 1984 to the above inventors, 2-guanidino-4-(2-substituted-amino-4-imidazolyl)thiazoles are disclosed which are of the formula (XIII) wherein X is N, Y is CH and R is NH$_2$, optionally monosubstituted or disubstituted by certain alkyl or phenylalkyl groups, useful in treatment of peptic ulcers.

SUMMARY OF THE INVENTION

The present invention relates to novel 2-(N-substitutedguanidino)-4-heteroarylthiazoles of the formula

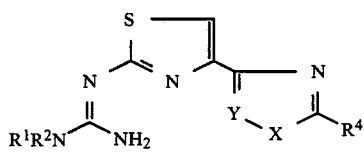

(I)

or a pharmaceutically acceptable acid addition salt thereof, wherein either X is NH and Y is CH or N, or X is S and Y is CH;

R$^1$ is (C$_4$–C$_{10}$)alkyl which can be a straight or branched chain group, or R$^1$ is (R$^3$)$_2$C$_6$H$_3$ or (R$^3$)$_2$Ar(CH$_2$)$_n$, where n is an integer from 1 to 4, the R$^3$ groups are the same or different and are H, F, Cl, Br, I, CH$_3$, CH$_3$O, NO$_2$, NH$_2$, OH, CN, COOR$^5$ or OCOR$^5$ and R$^5$ is (C$_1$–C$_3$)alkyl; and Ar is the residue of a phenyl, naphthyl, furyl, thienyl, pyridyl, pyrimidinyl, thiazolyl or imidazolyl group;

R$^2$ is H or (C$_1$–C$_4$)alkyl; or when R$^1$ and R$^2$ are taken together with the nitrogen atom to which they are attached, they form a pyrrolidino, piperidino, morpholino or 4-methylpiperazino group; and R$^4$ is H, (C$_1$–C$_5$)alkyl, NH$_2$ or CH$_2$OH.

In each case, above, the bracketed range of carbon atoms refers to the total number of carbon atoms in the group. The carbon chain can be straight or branched.

Pharmaceutically acceptable acid addition salts are those with from one to three equivalents of the acid, and especially with one or two equivalents. Suitable acids include, but are not limited to, HCl, HBr, H$_2$SO$_4$, H$_3$PO$_4$, CH$_3$SO$_3$H, p-toluenesulfonic acid, maleic acid, fumaric acid, succinic acid and citric acid. For a current list of such salts see, e.g. Berge et al., *J. Pharm. Sci.*, 66, 1-19 (1977).

Because of their facile preparation and high level of antisecretory activity, histamine-$H_2$ antagonist activity and/or cytoprotective activity as evidenced in tests for inhibition of ethanol-induced ulcers, preferred compounds of formula (I) are:

(1) of the formula

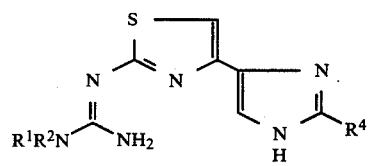

(IX)

wherein R$^1$, R$^2$ and R$^4$ are as previously defined. Particularly preferred such compounds are those wherein R$^1$ is said alkyl, (R$^3$)$_2$C$_6$H$_3$ or (R$^3$)$_2$Ar(CH$_2$)$_n$ where one R$^3$ is H and the other is H, CH$_3$O or Cl and Ar is phenyl, furyl, thienyl, pyridyl or naphthyl. Especially preferred compounds of formula (IX) are those wherein R$^1$ is n-pentyl, n-hexyl, n-heptyl, n-octyl, 2-octyl, phenyl, benzyl, phenylethyl, phenylpropyl, phenylbutyl, 4-chlorobenzyl, 4-chlorophenylethyl, 4-chlorophenylpropyl, 4-methoxybenzyl, 4-methoxyphenylethyl, furylmethyl, thienylmethyl, 3-pyridylmethyl, 1-naphthylmethyl or 2-naphthylmethyl; R$^2$ is H, and R$^4$ is said alkyl, especially CH$_3$;

(2) of the formula

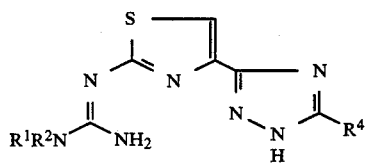

(VII)

wherein R$^1$ is said alkyl, (R$^3$)$_2$C$_6$H$_3$ or (R$^3$)$_2$Ar(CH$_2$)$_n$ where Ar is the residue of a phenyl group; especially preferred $R^1$ are n-hexyl, 2-octyl or benzyl, $R^2$ is H and $R^4$ is H, $CH_3$ or $NH_2$;

(3) of the formula

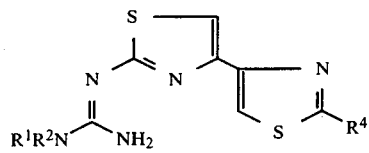
(VIII)

wherein $R^1$, $R^2$ and $R^4$ are as defined for compounds (VII), above.

The present invention further relates to a pharmaceutical composition for inhibiting gastric ulcers in a mammal, including a human, which comprises a pharmaceutically acceptable diluent or carrier and a gastric ulcer inhibiting amount of a compound of formula (I). Additionally, the invention relates to a method of inhibiting gastric ulcers in a mammalian subject in need of such treatment which comprises administering to the subject a gastric ulcer inhibiting amount of a compound of formula (I).

The most particularly preferred invention compounds are:

N-[4-(2-methylimidazol-4-yl)thiazol-2-yl]-N'-n-hexylguanidine;

N-[4-(2-methylimidazol-4-yl)thiazol-2-yl]-N'-2-octylguanidine;

N-[4-(2-methylimidazol-4-yl)thiazol-2-yl]-N'-benzylguanidine;

N-[4-(2-methylimidazol-4-yl)thiazol-2-yl]-N'-(2-furylmethyl)guanidine;

N-[4-(2-methylimidazol-4-yl)thiazol-2-yl]-N'-(2-thienylmethyl)guanidine; or an acid addition salt of any of the above compounds.

DETAILED DESCRIPTION OF THE INVENTION

The 2-(N-substitutedguanidino)-4-(imidazol-4-yl)thiazole and the 2-(N-substitutedguanidino)-4-(thiazol-4-yl)thiazole compounds of the invention of formula (VI) are prepared, for example, by the following reaction scheme:

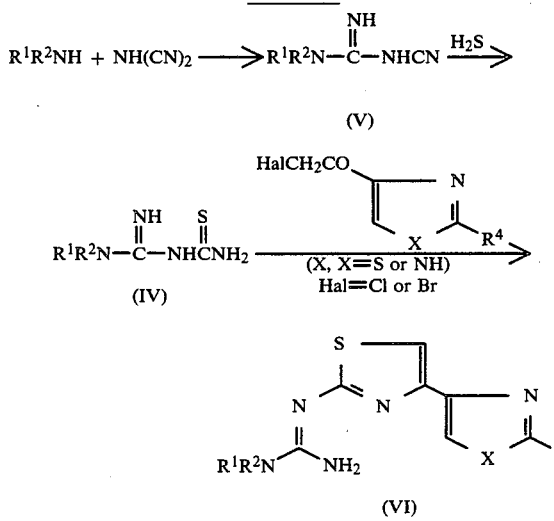

The 2-(N-substitutedguanidino)-4-(1,2,4-triazol-5-yl)thiazole compounds of the invention of formula (VII) are prepared, e.g., by the method shown below:

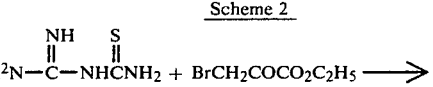

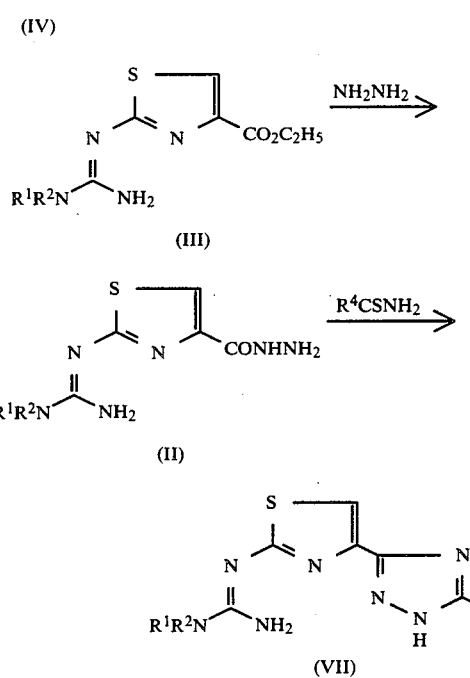

In the first step of Scheme 1, the preparation of the N-cyanoguanidine compounds (V) are prepared by reaction of the appropriate amine and dicyanimide in approximately equimolar amounts by methods previously described by Curd et al., *J. Chem. Soc.*, 1630 (1948) and by Redmon and Nagy in U.S. Pat. No. 2,455,807. Typically, the reactants are heated in the presence of a polar organic solvent, e.g. a ($C_1$-$C_4$)alkanol, water or mixtures thereof, preferably n-butanol, at a temperature of from 40° to 120° C., preferably at the reflux temperature of the solvent. The N-cyanoguanidine product is then isolated, e.g. by cooling, filtering to remove precipitated salts and evaporation of the filtrate.

The guanylthiourea intermediates (IV) are obtained by reaction of the appropriate N-cyanoguanidine with hydrogen sulfide. This reaction is ordinarily carried out in the presence of a polar organic solvent such as a ($C_1$-$C_4$)alkanol, acetone, ethyl acetate or dimethylsulfoxide, a preferred solvent is methanol. Typically, the reaction is carried out in the presence of a catalytic amount of a secondary amine, preferably diethylamine. The reaction can be carried out at atmospheric pressure or a higher pressure, e.g. at 3 to 10 atmospheres, and at a temperature of from about 10° to 100° C., preferably from 25° to 80° C. Of course, when the reaction is run at a higher temperature within the preferred range, the reaction time will be shorter. Conversely, at a lower temperature the reaction time required will be longer. The product is ordinarily isolated simply by evaporation of solvent. In many cases the crude product, thusly obtained, is of sufficient purity for use in the next reaction step. Alternatively, the crude product can be purified, e.g. by column chromatography.

In the third step of Scheme 1 an N-substitutedguanylthiourea compound (IV) is reacted with a molar equivalent of a 2-($R^4$-substituted)-4-haloacetylimidazole or 2-($R^4$-substituted)-4-haloacetylthiazole intermediate of formula (X). While the halogen atom in the above compounds can be chloro or bromo, the latter is ordinarily preferred. The reaction is carried out in the presence of a reaction-inert organic solvent such as tetrahydrofuran, a lower alkanol such as methanol, ethanol or isopropanol; a lower alkyl ketone such as acetone or methylethyl ketone, dimethylsulfoxide or dimethylformamide. Preferred solvents are acetone and dimethylformamide. A preferred temperature for preparation of the invention compounds (VI) by the above reaction is from about 20° to 120° C., and especially from about 50° to 60° C. The compound (VI) is then isolated by methods well known in the art, e.g. by cooling to form a precipitate, evaporation of solvent or by addition of a nonsolvent such as ethyl ether, to obtain the product as the hydrobromide salt. The hydrobromide salt is readily converted to the free base by standard neutralization/extraction methods. To obtain other pharmaceutically acceptable acid addition salts, in free base is taken up in an organic solvent and either one equivalent or at least two equivalents of the acid corresponding to the desired salts is added. The salt is then recovered by filtration, concentration or addition of a nonsolvent, or by a combination of these steps.

As shown in Scheme 2, above, the triazolylthiazole compounds of formula (VII) are obtained in three steps starting from the (N-substitutedguanyl)thiourea intermediate of formula (IV). The appropriate compound (IV) is condensed with an equimolar amount of an alkyl halopyruvate ester, preferably the readily available ethyl bromopyruvate, in the presence of a reaction inert organic solvent to form the corresponding 2-(substitutedguanidino)thiazole-4-carboxylate ester of formula (III). This reaction is carried out at a temperature of from about 40° to 120° C. and preferably at 60°–80° C. Examples of reaction inert solvents are the ($C_1$–$C_4$)-alkanols, acetone, ethyl acetate, acetonitrile, benzene or toluene and preferred solvents are said alkanols, especially ethanol in which the reaction is conveniently carried out at the reflux temperature. The product of formula (III) is isolated by standard methods such as evaporation/extraction and is purified, if desired, also by standard methods such as recrystallization or column chromatography on silica gel.

In the next step of Scheme 2 the compound of formula (III) is reacted with hydrazine or a salt or hydrate thereof. The latter reagent is ordinarily employed in a molar excess, e.g. a 10 to 40 mole excess. The resulting product is the corresponding acid hydrazide of formula (II). This step is also carried out in the presence of a reaction inert solvent such as, for example, those mentioned above for the previous reaction step. A preferred such solvent is ethanol for reasons of economy and efficiency. A preferred temperature for carrying out this step is from about 40° to 120° C. and especially 60°–80° C. When the preferred solvent, ethanol, is employed, the reaction is most conveniently carried out at the reflux temperature of the mixture. As in the previous step, the isolation of the acid hydrazide intermediate is by standard evaporation/extraction techniques.

In the final step of Scheme 2 the acid hydrazide is contacted with a thioamide of the formula $R^4CSNH_2$, where $R^4$ is as previously defined. This step is carried out in the presence of a reaction inert organic solvent, e.g. those disclosed above for the first step of this Scheme, and at a temperature in the range of from about 50° to 150° C. In a preferred such method this step is carried out in the presence of a molar excess, up to a 10 fold excess, of the thioamide, in n-butanol at the reflux temperature. Under these conditions the reaction is ordinarily complete in from 1 to 4 days, after which the 2-(N-substituted-guanidino)-4-(1,2,4-triazol-5-yl)thiazole compound of formula (VII) is isolated by standard techniques, such as evaporation of solvent and purification of the crude product, if desired, e.g. by crystallization or by column chromatographic methods.

The 2-($R^4$-substituted)-4-bromoacetylimidazole and corresponding 4-bromoacetylthiazole intermediates of formula (X) are prepared by reaction of the corresponding 4-acetyl compound

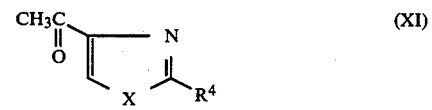

with elemental bromine in the presence of hydrogen bromide by well known procedures for halogenation of methyl ketones. Typically, approximately equimolar amounts of the ketone (XI), dissolved in aqueous 48% hydrogen bromide, and bromine are contacted at or about room temperature, then heated at 60°–80° C. for from two to six hours to complete the reaction. The bromacetyl compound (X) is then isolated by standard methods, e.g. evaporation of the reaction mixture and purification of the crude product is carried out by standard extraction and crystallization techniques.

The corresponding 4-chloroacetylimidazole and 4-chloroacetylthiazole intermediates of formula (X) where Hal is chloro are also prepared from the appropriate compound of formula (XI), typically by reaction with sulfuryl chloride. The compound (XI) is dissolved in methylene chloride, dry hydrogen chloride added optionally followed by methanol to dissolve the precipitated hydrochloride salt. An equimolar amount of sulfuryl chloride is then added at room temperature and the chloroketone isolated by standard methods.

The starting acetylthiazole compounds of formula (XI) where X is S are obtained, for example, by reaction of 1-bromo-2,3-butanedione with thiourea or a thioamide of the formula $R^4CSNH_2$ in equimolar amounts. Typically, the reaction is carried out in a reaction inert solvent, e.g. ethanol or isopropanol at a temperature of from 20° to 80° C., preferably at room temperature. The product of formula (XI) is isolated by standard methods known in the art.

The starting acetylimidazoles of formula (XI) where X is NH are prepared, for example, by methods disclosed by LaMattina and Lipinski in U.S. Pat. No. 4,374,843 and methods disclosed in U.S. patent application Ser. No. 445,787 filed Dec. 1, 1982 and U.S. patent application Ser. No. 483,787 filed Apr. 11, 1983, both of which are assigned to the same assignee as the instant application.

The starting alkylamines of formula $R^1R^2NH$ are commercially available. The requisite starting aniline compounds, $(R^3)_2C_6H_3NH_2$ and aralkylamines, $(R^3)_2AR(CH_2)_nNH_2$ are either commercially available or are prepared by methods well known to those of skill in the art. The aralkylamines wherein n is 1 are prepared, for example, by reduction of the corresponding nitrile with hydrogen and a noble metal catalyst or by reduction with an alkali metal hydride such as lithium aluminum hydride by well known methods. The corresponding aralkylamines, $(R^3)_2ArCH_2CH_2NH_2$ can be prepared by a number of known methods, for example, by reaction of the corresponding halomethyl compound, $(R^3)_2ArCH_2Cl(Br)$ with sodium cyanide to provide an arylacetonitrile intermediate which is then hydrogenated to the desired 2-arylethylamine by the methods described above.

Reaction of the appropriate aldehyde, $(R^3)_2ArCHO$ or its acetal with a 2-cyanoacetate ester followed by hydrolysis and decarboxylation provides a 3-arylacrylonitrile intermediate which can be reduced stepwise to give the corresponding amine, $(R^3)_2Ar(CH_2)_3NH_2$.

The 4-arylbutylamines are prepared, for example, from the appropriate aldehyde, $(R^3)_2ArCHO$, by reaction with Wittig reagent prepared from 3-bromopropionic acid to afford the corresponding 4-aryl-3-butenoic acid which is reduced to the corresponding 4-arylbutyric acid. This is then converted to the amide which is hydrogenated, e.g. by a metal hydride to form the desired 4-arylbutylamine.

The secondary amines of formula $(R^3)_2Ar(CH_2)_nNHR^2$ where $R^2$ is $(C_1-C_4)$alkyl are prepared by alkylation of the corresponding primary amine by well known methods, e.g., by reaction with $(C_1-C_4)$alkyl halides or alkyl sulfates or catalytic hydrogenation of the appropriate Schiff base, e.g. $(R^3)_2Ar(CH_2)_nNH=CH(CH)_2CH_3$.

The pharmaceutically acceptable acid addition salts of the novel compounds of formula I are also embraced by the present invention. The salts are readily prepared by contacting the free base with an appropriate mineral or organic acid in either aqueous solution or in a suitable organic solvent. The solid salt may then be obtained by precipitation or by evaporation of the solvent. Especially preferred salts are the hydrochloride and dihydrochloride.

The antiulcer utility of the compounds of the formula (I) in mammals, including man, is reflected in their antisecretory, histamine-$H_2$ antagonist and/or inhibition of ethanol-induced ulcers in rats, as detailed in the Examples below. To inhibit (prevent or treat) gastric ulcers in a mammalion subject, the products of the present invention are administered by a variety of conventional routes of administration including orally and parenterally. Preferably, the compounds and administered orally. In general, these compounds will be administered orally at doses between about 0.1 and 20 mg/kg body weight of the subject to be treated per day, preferably from about 0.2 to 2.5 mg/kg per day, in single or divided doses. If parenteral administration is desired, then these compounds can be given at total daily doses between about 0.1 and 1.0 mg/kg body weight of the subject to be treated. However, at the discretion of the attending physician, some variation in dosage will necessarily occur, depending upon the condition of the subject being treated and the particular compound employed.

The compound is administered alone or in combination with pharmaceutically acceptable carriers or diluents, in either single or multiple doses. Suitable pharmaceutical carriers include inert diluents or fillers, sterile aqueous solutions and various organic solvents. The pharmaceutical compositions formed by combining the novel compounds of formula (I) or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Preferably, the products of this invention are administered orally in unit dosage form, i.e. as a single physically discrete dosage unit containing an appropriate amount of the active compound in combination with a pharmaceutically acceptable carrier or diluent. Examples of such unit dosage forms are tablets or capsules containing from about 5 to 1,000 mg of the active ingredient, the compound of formula (I) comprising from about 10% to 90% of the total weight of the dosage unit.

For parenteral administration, solutions or suspensions of the compound of formula (I) in sterile aqueous solutions, for example aqueous propylene glycol, sodium chloride, dextrose or sodium bicarbonate solutions are employed. Such dosage forms are suitably buffered if desired. The preparation of suitable sterile liquid media for parenteral administration will be well known to those skilled in the art.

The present invention is illustrated by the following examples. However, it should be understood that the invention is not limited to the specific details of these examples. All temperatures are in degrees centigrade. Nuclear magnetic resonance spectra (NMR) were measured for solutions in deuterated chloroform ($CDCl_3$) deuterated methanol ($CD_3OD$) or deuterated dimethyl sulfoxide ($DMSO-d_6$), and peak positions are reported in parts per million downfield from tetramethylsilane. The following abbreviations for peak shapes are used: bs, broad singlet; s, singlet; d, doublet; t, triplet; q, quartet, m, multiplet.

EXAMPLE 1

Ethyl 2-(1-n-hexyl-3-guanidino)thiazole-4-carboxylate

A mixture of 1-(n-hexylguanyl)thiourea (4.05 g, 20 mmole) ethyl bromopyruvate (4.09 g, 21 mmole) and 200 ml ethanol was heated at reflux for 4 hours and cooled. The mixture was concentrated in vacuo to a yellow solid which was treated with saturated sodium bicarbonate solution and extracted with chloroform. The dried extracts were concentrated in vacuo to an orange oil which solidified upon trituration with hexane. After recrystallization from hexane/ethyl acetate 3.72 g (62%) of yellow crystals was obtained. Workup of the mother liquors gave an additional 1.20 g (20%) of product. An analytical sample was obtained by recrystallization from hexane ethyl/acetate, m.p. 118°–119° C. Mass spectrum (m/e): 298 (M+); $^1$H-NMR (CDCl$_3$)ppm(delta): 0.6–1.8 (m, 14H), 3.2 (m, 2H), 4.3 (q, J=7H$_2$, 2H), 7.03 (s, br., 3H), 7.41 (s, 1H).

Analysis Calculated for C$_{13}$H$_{22}$N$_4$O$_2$S: C, 52.32; H, 7.43; N, 18.78%. Found: C, 52.41; H, 7.55; N, 18.36%.

EXAMPLE 2

2-(1-n-Hexyl-3-guanidino)thiazole-4-carboxylic acid hydrazide

A mixture of 3.36 g (11.3 mmole) ethyl 2-(1-n-hexyl-3-guanidino)thiazole-4-carboxylate and 6.5 ml (110 mmole) 85% hydrazine hydrate in 110 ml ethanol was heated at reflux for 24 hours. An additional 6.5 ml hydrazine hydrate was added and heating continued for another 24 hours. The resulting mixture was cooled, solvent evaporated in vacuo, the residual colorless solid was triturated with isopropanol and filtered to yield 2.52 g (78%) of colorless powder. An analytical sample was obtained upon recrystallization from isopropanol, m.p. 136°–137° C. Mass spectrum (m/e): 284 (M+); $^1$H-NMR(DMSO-d$_6$/CD$_3$OD)ppm(delta): 0.7–1.7 (m, 11H), 3.2 (m, 2H), 7.31 (s, 1H).

Analysis Calculated for C$_{11}$H$_{20}$N$_6$OS: C, 46.45; H, 7.09; N, 29.55%. Found: C, 46.16; H, 7.18; N, 29.93%.

EXAMPLE 3

2-(1-n-Hexyl-3-guanidino)-4-(3-methyl-1H-1,2,4-triazol-5-yl)thiazole (VII, R$^1$=n-C$_6$H$_{13}$, R$^2$=H, R$^4$=CH$_3$)

A mixture of 568 mg (2.0 mmole) 2-(1-n-hexyl-3-guanidino)thiazole-4-carboxylic acid hydrazide, 751 mg (10 mmole) thioacetamide in 20 ml n-butanol was heated at reflux for 48 hours. The cooled reaction mixture was concentrated in vacuo and the residue chromatographed on a silica gel column to give 241 mg (39%) of the pure triazole as a yellow foam, m.p. 207°–209° C. Mass spectrum (m/e): 307 (M+); $^1$H-NMR (CD$_3$OD)ppm(delta): 0.7–1.8 (m, 11H), 2.43 (s, 3H), 3.3 (m, 2H), 7.22 (s, 1H).

Analysis calculated for C$_{13}$H$_{21}$N$_7$S.0.5H$_2$O: C, 49.34; H, 7.01; N, 30.99%. Found: C, 49.42; H, 6.73; N, 30.82%.

EXAMPLE 4

2-(1-n-Hexyl-3-guanidino)-4-(3-amino-1H-1,2,4-triazol-5-yl)thiazole (VII, R$^1$=n-C$_6$H$_{13}$, R$^2$=H, R$^4$=NH$_2$)

A mixture of 852 mg (3.0 mmole) 2-(1-n-hexyl-3-guanidino)thiazole-4-carboxylic acid hydrazide, 835 mg (3.0 mmole) S-methylisothiouronium sulfate and 492 mg (6.0 mmole) sodium acetate in 30 ml n-butanol was heated at reflux for four hours and cooled. The resulting mixture was filtered, the filtrate concentrated in vacuo and the residue chromatographed twice on silica gel columns, first eluting with 85:15 chloroform/methanol, then with acetone, to afford 491 mg (53%) of title compound as a yellow solid, m.p. 210°–211° C. Mass spectrum (m/e): 308 (M+); $^1$H-NMR(CD$_3$OD)ppm(delta): 0.7–1.9 (m, 11H), 3.2 (m, 2H), 7.13 (s, 1H).

Analysis calculated for C$_{12}$H$_{20}$N$_8$S: C, 46.73; H, 6.54; N, 36.34%. Found: C, 46.63; H, 6.42; N, 36.03%.

EXAMPLE 5

2-(N-Hexyl-N'-guanidino)-4-(2-methylimidazol-4-yl)thiazole dihydrochloride

A. To a solution of 13.08 g (46.05 mmole) 2-bromo-1-(2-methylimidazol-4-yl)ethanone hydrobromide in 150 ml acetone was added a solution of 10.25 g (50.66 mmole) 1-(n-hexylguanyl)thiourea in 50 ml acetone, the mixture refluxed for six hours and allowed to stand at room temperature for 16 hours. The mixture was heated at reflux for an additional hour, cooled and the product collected to give 19.44 g (90%) of yellow solid (dihydrobromide salt). This was dissolved in 300 ml water and added to a solution of 20.59 g (166 mmole) sodium carbonate monohydrate in 200 ml water. After standing for 15 minutes the solid was filtered and washed with water. The damp solid was dissolved in 400 ml acetone, filtered to remove insoluble material, and the filtrate treated with 8 ml 37% (w/v) concentrated hydrochloric acid. The acidified mixture was stirred for 1.5 hours, filtered and the collected solid dried to yield 16.31 g of light yellow solid. This was dissolved in 50 ml methanol, carbon treated and filtered through diatomaceous earth. The filtrate was diluted with isopropyl ether and the solid precipitate collected by filtration and dried to afford 11.50 g (66%) of the desired product as a light yellow powder, m.p. 303°–305° C. Mass spectrum (m/e): 306 (M+); $^1$H-NMR(DMSO-d$_6$)ppm(delta): 0.7–1.8 (m, 11H), 2.70 (s, 3H), 3.25 (m, 2H), 7.83 (s, 1H), 8.03 (s, 1H), 8.6 (m, 3H).

Analysis calculated for C$_{14}$H$_{22}$N$_6$S.2HCl: C, 44.32; H, 6.38; N, 22.15%. Found: C, 43.83; H, 6.29; N, 21.89%.

B. When the above procedure was repeated, but with 114 mg (0.71 mmole) of 4-chloroacetyl-2-methylimidazole, 144 mg (0.71 mmole) 1-(n-hexylguanyl)thiourea and 8 mmole hydrogen chloride in 7 ml acetone and heating at reflux for 65 hours, a 36% yield of the desired product was obtained as a tan powder.

EXAMPLE 6

By employing the appropriate N-substituted guanylthiourea in place of 1-(n-hexylguanyl)thiourea in the procedure of Example 5 the following compounds of the formula below are obtained as acid addition salts.

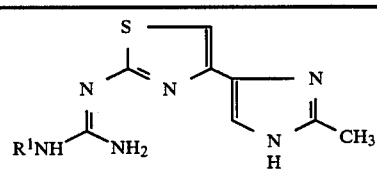

| R$^1$ | Salt* | m.p., °C. | Mass Spectrum (M+) | Elemental Analysis % | |
|---|---|---|---|---|---|
| | | | | Calc'd | Found |
| a. C$_6$H$_5$CH$_2$ | 2HCl | 306–307° | 312 | C, 46.75 | C, 46.48 |

-continued

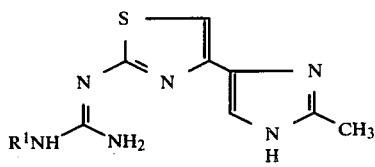

| $R^1$ | Salt* | m.p., °C. | Mass Spectrum (M+) | Elemental Analysis % Calc'd | Found |
|---|---|---|---|---|---|
| | | (81% yield) white solid | | H, 4.71<br>N, 21.81<br>Cl, 18.40 | H, 4.82<br>N, 21.94<br>Cl, 18.04 |
| b. CH$_3$(CH$_2$)$_5$CH(CH$_3$) | 2HCl | 62–64° (68% yield) from THF | 334 | C, 47.16<br>H, 6.93<br>N, 20.63 | C, 46.76<br>H, 6.89<br>N, 20.51 |
| c. CH$_3$(CH$_2$)$_4$ | 2HBr.H$_2$O | 274–276° | 292 | C, 33.06<br>H, 5.12<br>N, 17.80 | C, 33.47<br>H, 5.40<br>N, 17.83 |
| d. CH$_3$(CH$_2$)$_3$ | 2HBr.H$_2$O | 254–256° | 278 | C, 31.45<br>H, 4.84<br>N, 18.34 | C, 31.57<br>H, 5.15<br>N, 18.11 |
| e. CH$_3$(CH$_2$)$_5$ | 2HBr | 282–284° | 306 | C, 35.91<br>H, 5.16<br>N, 17.94 | C, 35.79<br>H, 5.24<br>N, 17.93 |
| f. CH$_3$(CH$_2$)$_6$ | 2HBr | 280–282° | 320 | C, 37.35<br>H, 5.43<br>N, 17.43 | C, 37.07<br>H, 5.42<br>N, 17.03 |
| g. CH$_3$(CH$_2$)$_7$ | 2HBr | 284–286° | 334 | C, 38.72<br>H, 5.69<br>N, 16.93 | C, 38.30<br>H, 5.70<br>N, 16.75 |
| h. CH$_3$(CH$_2$)$_8$ | 2HBr | 290–292° | 348 | C, 40.01<br>H, 5.93<br>N, 16.47 | C, 39.99<br>H, 6.03<br>N, 16.49 |
| i. CH$_3$(CH$_2$)$_4$CH(CH$_3$) | 2HBr | 208–209° | 320 | C, 37.35<br>H, 5.43<br>N, 17.43 | C, 37.06<br>H, 5.26<br>N, 17.26 |
| j. CH$_3$(CH$_2$)$_5$CH(CH$_3$) | 2HBr.H$_2$O | 174–176° | 334 | C, 37.36<br>H, 5.88<br>N, 16.34 | C, 37.73<br>H, 5.98<br>N, 16.59 |
| k. C$_6$H$_5$ | 2HBr.1.5H$_2$O | 70° | 298 | C, 34.51<br>H, 3.93<br>N, 17.25 | C, 34.72<br>H, 4.05<br>N, 17.18 |
| l. C$_6$H$_5$CH$_2$ | 2HBr | 273–275° | 312 | C, 37.99<br>H, 3.83<br>N, 17.72 | C, 37.62<br>H, 3.84<br>N, 17.48 |
| m. C$_6$H$_5$(CH$_2$)$_2$ | 2HBr | 290–292° | 326 | C, 39.36<br>H, 4.13<br>N, 17.21 | C, 39.07<br>H, 4.20<br>N, 17.04 |
| n. C$_6$H$_5$(CH$_2$)$_3$ | 2HBr.H$_2$O | 264–266° | 340 | C, 39.24<br>H, 4.65<br>N, 16.15 | C, 39.49<br>H, 4.59<br>N, 16.15 |
| o. C$_6$H$_5$(CH$_2$)$_4$ | 2HBr | 259–261° | 354 | C, 41.87<br>H, 4.69<br>N, 16.28 | C, 41.45<br>H, 4.81<br>N, 16.15 |
| p. 4-ClC$_6$H$_4$CH$_2$ | 2HBr | 297–298° | 346 | C, 35.41<br>H, 3.37<br>N, 16.52 | C, 35.21<br>H, 3.64<br>N, 16.29 |
| q. 4-ClC$_6$H$_4$(CH$_2$)$_2$ | 2HBr | 268–270° | 360 | C, 36.76<br>H, 3.66<br>N, 16.08 | C, 36.52<br>H, 3.96<br>N, 15.83 |
| r. 4-ClC$_6$H$_4$(CH$_2$)$_3$ | 2HBr | 243–245° | 374 | C, 38.04<br>H, 3.94<br>N, 15.66 | C, 38.01<br>H, 3.94<br>N, 15.60 |
| s. 4-CH$_3$OC$_6$H$_4$CH$_2$ | 2HBr | 264–266° | 342 | C, 38.11<br>H, 4.00<br>N, 16.67 | C, 37.75<br>H, 4.07<br>N, 16.56 |
| t. 4-CH$_3$OC$_6$H$_4$(CH$_2$)$_2$ | 2HBr | 249–251° | 356 | C, 39.39<br>H, 4.28<br>N, 16.22 | C, 39.05<br>H, 4.38<br>N, 16.01 |

-continued

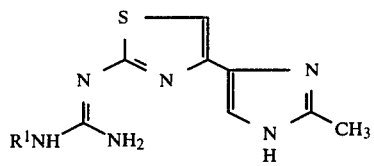

| $R^1$ | Salt* | m.p., °C. | Mass Spectrum (M+) | Elemental Analysis % Calc'd | Found |
|---|---|---|---|---|---|
| u. (thiophen-2-ylmethyl) | 2HBr | 226–228° | 318 | C, 32.51<br>H, 3.36<br>N, 17.50 | C, 32.13<br>H, 3.42<br>N, 17.03 |
| v. (furan-2-ylmethyl) | 2HCl | >325° | 302 | C, 41.60<br>H, 4.30<br>N, 22.40<br>Cl, 18.89 | C, 41.51<br>H, 4.51<br>N, 22.25<br>Cl, 18.74 |
| w. (pyridyl-CH$_2$) | 3HCl | >325° | 313 | C, 39.77<br>H, 4.29<br>N, 23.19<br>Cl, 25.16 | C, 39.39<br>H, 4.58<br>N, 21.94<br>Cl, 24.80 |
| x. 1-naphthylmethyl | 2HBr | 298–299° | 362 | C, 43.52<br>H, 3.85<br>N, 16.03 | C, 43.56<br>H, 3.92<br>N, 15.93 |
| y. 2-naphthylmethyl | 2HBr | 287–289° | 362 | C, 43.52<br>H, 3.85<br>N, 16.03 | C, 43.64<br>H, 3.99<br>N, 16.06 |

*The hydrobromide salts were prepared by using 48% hydrobromic acid in place of hydrochloric acid.

EXAMPLE 7

2-(N-n-Hexyl-N'-guanidino)-4-(imidazol-4-yl)thiazole Dihydrobromide (VI, $R^1$=n-$C_6H_{13}$, $R^2$,$R^4$=H)

A solution of 511 mg (4.64 mmole) 4-acetylimidazole in 6 ml acetic acid was treated with 1 ml (9 mmole) 48% hydrobromic acid and then with 741 mg (4.64 mmole) bromine in 4 ml acetic acid. The mixture was stirred at 50° C. for four hours, 938 mg (4.64 mmole) 1-(n-hexylguanyl)thiourea was added and stirring continued for 20 hours at 50° C. The cooled reaction mixture was diluted with acetone and filtered to obtain 735 mg (35%) of title compound as a white powder, m.p. 254°–255° C. Mass spectrum (m/e): 292 (M+); $^1$H-NMR(DMSO-d$_6$) ppm(delta): 0.7–1.9 (m, 11H), 3.5 (m, 2H), 7.87 (s, 1H), 8.25 (s, 1H), 8.6 (s, br, 3H), 9.28 (s, 1H).

Analysis calculated for $C_{13}H_{20}N_6S.2HBr$: C, 34.37; H, 4.88; N, 18.50%. Found: C, 34.24; H, 5.01; N, 18.48%.

EXAMPLE 8

2-(N-n-Hexyl-N'-guanidino)-4-(2-ethylimidazol-4-yl)thiazole Dihydrochloride (VI, $R^1$=n-$C_6H_{13}$, $R^2$=H, $R^4$=$C_2H_5$)

The procedure of the preceding Example was repeated but starting with 1.45 g (10.5 mmole) 4-acetyl-2-ethylimidazole, stirring 6 hours at 50° C. before adding an equimolar amount of 1-(n-hexylguanyl)thiourea and 20 hours at 50° C. after its addition. The reaction mixture was then concentrated in vacuo to a syrup, taken up in acetone and cooled to yield 1.58 g (31%) of pink solid. This was treated with saturated sodium bicarbonate solution, extracted with ethyl acetate, the extracts dried, concentrated and the residue purified by silica gel column chromatography. Product fractions were combined, concentrated to an oil, dissolved in 100 ml ethanol and treated with 2 ml 37% hydrochloric acid. Upon evaporation in vacuo a yellow solid was obtained which was triturated with acetone, filtered to afford 776 mg (19%) tan powder, m.p. 285°–287° C. Mass spectrum (m/e): 320 (M+); $^1$H-NMR(DMSO-d$_6$)ppm(delta): 0.7–2.0 (m, 14H), 3.05 (q, J=7 Hz, 2H), 3.5 (m, 2H), 7.88 (s, 1H), 8.02 (s, 1H), 8.7 (m, 3H).

Analysis calculated for $C_{15}H_{24}N_6S.2HCl$: C, 45.80; H, 6.66; N, 21.37%. Found: C, 45.42; H, 6.61; N, 21.10%.

EXAMPLE 9

4-(2-Aminothiazol-4-yl)-2-(1-n-hexyl-3-guanidino)-thiazole (VIII, $R^1$=n-$C_6H_{13}$, $R^2$=H, $R^4$=NH$_2$)

A. 2-Amino-4-bromoacetylthiazole hydrobromide

To a slurry of 1.11 g (5.0 mmole) 2-amino-4-acetylthiazole hydrobromide, prepared from 1-bromo-2,3-butanedione and thiourea by the method of Masaki et al., *Bull. Chem. Soc. Japan*, 39, 2745 (1966), in 50 ml acetic acid, was added 5 drops of 48% hydrobromic acid and 799 mg (5.0 mmole) bromine and the mixture warmed at 60° C. for one hour. The precipitated product was collected by filtration, washed with acetic acid and acetone to afford 1.32 g (88%) of light tan powder, m.p. 198° C. (dec. without melting). Mass spectrum (m/e): 220 (M+), 222 (M++2); $^1$H-NMR(DMSO-d$_6$)ppm(delta): 4.83 (s, 2H), 8.27 (s, 1H).

Analysis calculated for $C_5H_5N_2OSBr.HBr$: C, 19.88; H, 2.00; N, 9.28%. Found: C, 20.33; H, 2.04; N, 9.28%.

B. A mixture of 1.316 g (4.35 mmole) 2-amino-4-bromoacetylthiazole hydrobromide and 880 mg (4.35 mmole) 1-(n-hexylguanyl)thiourea in 44 ml dimethylformamide was heated at 60° C. for four hours. The cooled reaction mixture was concentrated in vacuo to an oil which was made alkaline by addition of 10% sodium carbonate solution and extracted with ethyl acetate. The dried extract was filtered, concentrated in vacuo and the residue twice chromatographed on silica gel columns, eluting with 9:1 chloroform/methanol. The purified product was recovered by evaporation of solvent, taken up in ethyl acetate and treated with excess hydrogen chloride gas. The resulting solid was collected and washed with ethyl acetate to yield 640 mg (37%) of the desired product as a colorless powder, m.p. 205°–207° C. (dec.). Mass spectrum (m/e): 324 (M+); $^1$H-NMR(DMSO-d$_6$) ppm(delta): 0.89 (m, 3H), 1.32 (m, 6H), 1.60 (m, 2H), 3.44 (m, 2H), 7.36 (s, 1H), 7.80 (s, 1H), 8.63 (s, br, 2H), 8.92 (s, br, 1H).

Analysis calculated for $C_{13}H_{20}N_6S_2.2HCl$: C, 39.29; H, 5.58; N, 21.15%. Found: C, 38.89; H, 5.56; N, 21.09%.

EXAMPLE 10

2-(1-n-Hexyl-3-guanidino)-4-(2-methylthiazol-4-yl)thiazole (VIII, $R^1$32 n-$C_6H_{13}$, $R^2$=H, $R^4$=CH$_3$)

A. 2-Acetyl-2-methylthiazole hydrobromide

An isopropanol solution of 1.13 g (15.0 mmole) thioacetamide and 2.47 g (15.0 mmole) 1-bromo-2,3-butanedione was stirred at room temperature for 10 days. The precipitated product was collected by filtration and washed with isopropanol to give 0.619 g (18%) of colorless powder. Evaporation of the filtrate and trituration of the residual solid with acetone afforded 2.329 g (70%) of yellowish powder, m.p. 200° C. (sublimes). Mass spectrum (m/e): 141 (M+); $^1$H-NMR (DMSO-d$_6$)ppm(delta): 2.60 (s, 3H), 2.78 (s, 3H), 8.42 (s, 1H).

Analysis calculated for $C_6H_7NOS.HBr$: C, 32.44; H, 3.63; N, 6.31%. Found: C, 32.41; H, 3.71; N, 6.29%.

B. 4-Bromoacetyl-2-methylthiazole hydrobromide

A slurry of 828 mg (3.73 mmole) 4-acetyl-2-methylthiazole hydrobromide in 37 ml acetic acid was treated with four drops of 48% hydrobromic acid and 596 mg (3.73 mmole) bromine and the mixture warmed to 60° C. After three hours at this temperature the mixture was allowed to cool to room temperature, a seed crystal added and allowed to stand overnight. The precipitated product was collected, washed with acetic acid and dried to afford 1.01 g (90%) of brown crystals, m.p. 187°–189° C. Mass spectrum (m/e): 219 (M+), 221 (M++2); $^1$H-NMR (DMSO-d$_6$)ppm(delta): 2.77 (s, 3H); 4.82 (s, 2H); 8.30 (s, 1H).

Analysis calculated for $C_6H_6NOSBr.HBr$: C, 23.94; H, 2.34; N, 4.65%. Found: C, 23.71; H, 2.30; N, 4.51%.

C. A mixture of 960 mg (3.19 mmole) 4-bromo-acetyl-2-methylthiazole hydrobromide, 645 mg (3.19 mmole) 1-(n-hexylguanyl)thiourea and 32 ml dimethylformamide was heated at 60° C. for four hours. The cooled mixture was diluted with ethyl ether and the precipitate collected to give 801 mg (52%) of off-white powder. Recrystallization gave 332 mg (21%), m.p. 160°–162° C. Mass spectrum (m/e): 323 (M+); $^1$H-NMR(DMSO-d$_6$)ppm (delta): 0.7–2.0 (m, 11H), 2.75 (s, 3H), 3.43 (m, 2H), 7.60 (s, 1H), 7.98 (s, 1H), 8.55 (s, br, 2H), 8.90 (s, br, 1H).

Analysis calculated for $C_{14}H_{21}N_5S_2.2HBr$: C, 34.64; H, 4.78; N, 14.43%. Found: C, 34.26; H, 4.68; N, 14.28%.

EXAMPLE 11

By reaction of the appropriate guanylthiourea selected from those provided in Preparation B with ethyl bromopyruvate, ethyl chloropyruvate or ethyl iodopyruvate by the method of Example 1, the following esters are obtained.

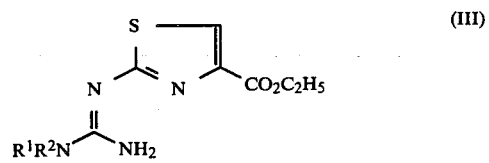
(III)

Use of methyl bromopyruvate, n-propyl bromopyruvate, isopropyl bromopyruvate or methyl chloropyruvate gave the corresponding methyl, n-propyl or isopropyl ester.

EXAMPLE 12

Reaction of the 2-guanidino thiazole-4-carboxylate esters provided in the preceding Example with hydrazine hydrate by the procedure of Example 2 affords the corresponding acid hydrazides of the formula

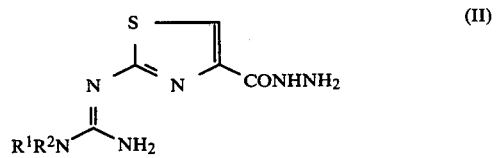
(II)

where $R^1$ and $R^2$ are as defined for the starting ester of formula (III).

EXAMPLE 13

A. Reaction of the appropriate acid hydrazide (II) provided in the preceding Example with thioacetamide by the method of Example 3 provides the corresponding 2-guanidino-4-(3-methyltriazol-5-yl)thiazoles of the formula below

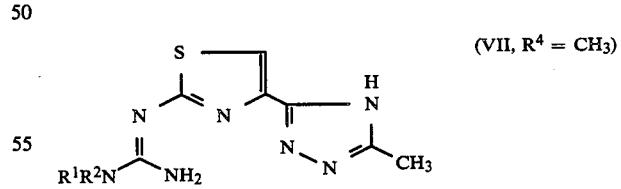
(VII, $R^4$ = CH$_3$)

wherein $R^1$ and $R^2$ are as defined for the starting compound of formula (II).

B. Similarly, use of the appropriate thioamide,

or isothiouronium salt in the above procedure yields the corresponding compounds of the formula

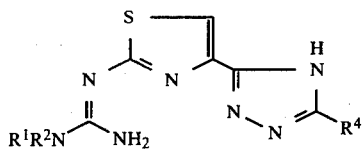

(VII)

where $R^4$ is H, $CH_3$, $CH_3CH_2$, $(CH_3)_2CH$, $CH_3(CH_2)_2$, n-$C_4H_9$, $NH_2$ or $HOCH_2$.

EXAMPLE 14

By repeating the procedure of Example 10 but employing the appropriate N-substituted or N,N-disubstituted guanylthiourea in place of 1-(n-hexylguanyl)thiourea in Part C, affords the following compounds

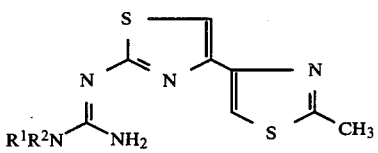

where $R^1$ and $R^2$ are as defined in Preparation B.

EXAMPLE 15

By employing the above method but with the appropriate 4-bromoacetyl-2-$R^4$-substituted thiazole as starting material, the corresponding compounds of the formula below are obtained.

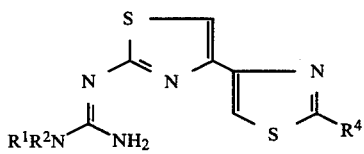

where $R^1$ and $R^2$ are as defined in Preparation B and $R^4$ is H, $CH_3$, $CH_3CH_2$, $CH_3(CH_2)_2$, $CH_3(CH_2)_3$, $(CH_3)_2CH(CH_3)_3$, $CH_3(CH_2)_5$, $CH_2OH$ or $NH_2$.

EXAMPLE 16

Gastric Acid Antisecretory Activity

The gastric acid antisecretory activity of compounds of the present invention was determined in overnight fasted, conscious Heidenhain pouch dogs. Pentagastrin (Pentavolon-Ayerst) was used to stimulate acid output by continuous infusion into a superficial leg vein at doses earlier determined to stimulate near maximal acid output from the gastric pouch. Gastric juice was collected at 30 minute intervals following the start of a pentagastrin infusion and measured to the nearest 0.1 ml. Ten collections were taken for each dog during an experiment. Acid concentration was determined by tritrating 1.0 ml of gastric juice to pH 7.4 with 0.1N sodium hydroxide using an Autoburette and a glass electrode pH meter (Radiometer).

Drug or vehicle was given intravenously or orally 90 minutes following the start of the pentagastrin infusion, at a dose of 2 mg/kg or less. Gastric acid antisecretory effects were calculated by comparing the lowest acid output after drug administration with the mean acid output immediately before drug.

The Example 6 products f, g, n and o at an oral dose of 2 mg/kg, inhibited gastric secretion at least 24%. Preferred products of Example 5* and Example 6a* b*, c, j, l and m inhibited gastric secretion at least 64% at the same or a lower dose. At a dose of 0.1 mg/kg (i.v.), the compound of Example 5* gave 58% inhibition.
*Tested as the dihydrobromide salt.

EXAMPLE 17

Histamine-$H_2$ Antagonist Activity

The histamine-$H_2$ antagonist activity of compounds of the present invention was determined by the following procedure:

Guinea pigs are killed rapidly with a blow to the head, the heart removed and the right atria dissected free. Atria are suspended, isometrically, in a temperature-controlled (32°±2° C.) tissue bath (10 ml) containing oxygenated (95% $O_2$; 5% $CO_2$) Krebs-Henseleit buffer (pH 7.4) and are allowed to stabilize approximately one hour during which time the tissue bath is flushed several times. Individual atrial contractions are followed with a force-displacement transducer connected to a cardiotachometer and Grass polygraph recorder. After obtaining a dose-response curve to histamine, the bath containing each atrium is flushed several times with fresh buffer and the atria reequilibrated to basal rates. Following the return to basal rate, test compounds are added at selected final concentrations and the histamine dose-response curve is again determined in the presence of antagonist. Results are expressed as dose-ratios, the ratio of histamine concentrations required to produce one-half of maximal stimulation in the presence and absence of antagonist, and the apparent dissociation constant of the $H_2$-receptor antagonist $pA_2$, is determined.

The compound of Example 5* and Example 6 products a*, b*, c, f, g, j and l-o all gave $pA_2$ values of at least 6.9. Preferred compounds of Example 5 and Example 6 products a*, b*, f, j, l, m and n gave $pA_2$ values of at lest 7.2.
*Tested as the dihydrobromide salt.

EXAMPLE 18

Inhibition of Ethanol-Induced Ulceration in Rats

The antiulcer activity of the products of this invention was also determined by an ethanol-induced rat ulcer assay. In this test, overnight fasted male rats are given drug (at 30 or 3 mg/kg) or water orally fifteen minutes prior to an orally administered dose of absolute ethanol (1.0 ml). One hour after the ethanol challenge the animals (8/group) are killed and the stomachs examined for the presence of lesions. After sacrifice the abdomen is opened and a locking hemostat placed at the pylorus. Six ml of a 4% solution of formaldehyde was injected into the stomach with a gastric feeding tube and a second locking hemostat was used to seal the esophagus. The stomach was removed, opened along the greater curvature and examined for ulceration.

The scoring system used to quantitate the ethanol-induced lesions is given below.

| Score | Ulcer Score Table Definition |
|---|---|
| 1 | Normal appearing stomach |
| 2 | Pinpoint sized lesions |
| 3 | Lesions, 2 or fewer; pinpoint lesions may be present |
| 4 | Lesions, >2; pinpoint lesions may be present |

| Ulcer Score Table | |
|---|---|
| Score | Definition |
| 5 | Lesions with hemorrhage |

For each group of animals an ulcer index is calculated as follows:

Ulceration Index = (the sum of the scores of the group) × (the sum of the number of ulcers in the group) × (the fraction of the group having any incidence of ulceration).

The percentage inhibition of ulcers is calculated as follows:

% Inhibition = 100 × [(ulcer index controls) − (ulcer index drug-treated)] ÷ (ulcer index controls).

At an oral dose of 30 mg/kg, the compound of Example 5 and Example 6 products a to c, f, j, l, m and o showed at least 77% inhibition of ethanol-induced ulceration. At the same dosage, Example 6 compounds c, f and o demonstrated 90% or better cytoprotection. At an oral dose of 3 mg/kg the compound of Example 5* and Example 6 products a*, b*, f, j and l showed at least 40% inhibition and those of Example 5* and 6 f gave at least 48% inhibition.
*Tested as the dihydrobromide salt.

PREPARATION A

General method for preparation of N-substituted-3-cyanoguanidines (V).

$$R^1R^2NH + HN(CN)_2 \longrightarrow R^1R^2NC=NCN \atop NH_2 \quad (V)$$

(i) 1-n-Hexyl-3-cyanoguanidine, (V, $R^1$=n-$C_6H_{13}$, $R^2$=H)

A mixture of 13.8 g (0.10 mole) n-hexylamine hydrochloride, 8.9 g (0.125 mole) dicyanimide and 75 ml n-butanol were stirred while heating at reflux for three hours. The mixture was then cooled; filtered to remove precipitated salt and the filtrate evaporated to a syrup and crystallized from dioxan. Mass spectrum (m/e): 169 molecular ion.

(ii) The following N-substituted-3-cyanoguanidines of the formula below are prepared from the appropriate amine, $R^1R^2NH$, by the above procedure.

$$R^1R^2C=NCN \atop NH_2 \quad (V)$$

| $R^1$ | $R^2$ | Mass Spectrum Molecular Ion (m/e) |
|---|---|---|
| n-Butyl | H | 141 |
| n-Pentyl | H | 155· |
| n-Heptyl | H | 183 |
| n-Octyl | H | 197 |
| n-Nonyl | H | 211 |
| 2-Heptyl | H | 183 |
| 2-Octyl | H | 197 |
| $C_6H_5$ | H | 160 |
| $C_6H_5CH_2$ | H | 175 |
| $C_6H_5(CH_2)_2$ | H | 188 |
| ·$C_6H_5(CH_2)_3$ | H | 201 |
| $C_6H_5(CH_2)_4$ | H | 217 |
| 4-$ClC_6H_4CH_2$ | H | 208 |
| 2-$ClC_6H_4(CH_2)_2$ | H | 222 |
| 4-$ClC_6H_4(CH_2)_3$ | H | 237 |
| 4-$CH_3OC_6H_4CH_2$ | H | 204 |
| 4-$CH_3OC_6H_4(CH_2)_2$ | H | 218 |
| 2-thienylmethyl | H | 180 |
| n-hexyl | $CH_3$ | 183 |
| —$(CH_2)_5$— | | 152 |
| 1-naphthylmethyl | H | 224 |
| 2-naphthylmethyl | H | 224 |
| 2-furylmethyl | H | 164 |
| 3-pyridylmethyl | H | 175 |

(iii) By employing the appropriate amine, $R^1R^2NH$ and dicyanimide, $HN(CN)_2$ in the above procedure yields the corresponding compounds $$R^1R^2NC=NCN. \atop NH_2$$

| $R^1$ | $R^2$ |
|---|---|
| $CH_3(CH_2)_9$ | H |
| $(CH_3)_2CH(CH_2)_7$ | H |
| $(CH_3)_2CH(CH_2)_5$ | $CH_3$ |
| $CH_3(CH_2)_5C(CH_3)_2$— | $C_2H_5$ |
| $(CH_3)_2CH(CH_2)_2$ | i-$C_3H_7$ |
| $CH_3CH(CH_3)(CH_2)_3$ | n-$C_4H_9$ |
| 2-$BrC_6H_4$ | H |
| 3-$BrC_6H_4CH_2$ | $CH_3$ |
| 4-$IC_6H_4(CH_2)_2$ | $CH_3$ |
| 2-$CH_3C_6H_4(CH_2)_3$ | $C_2H_5$ |
| 3-$NO_2C_6H_4(CH_2)_4$ | n-$C_3H_7$ |
| 4-$NH_2C_6H_5$ | H |
| 3-$HOC_6H_4CH_2$ | $CH_3$ |
| 4-$FC_6H_4$ | sec-$C_4H_9$ |
| 4-$CNC_6H_4$ | $CH_3$ |
| 4-$(COOCH_3)C_6H_4$ | H |
| 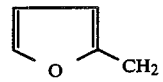 | $CH_3$ |
| 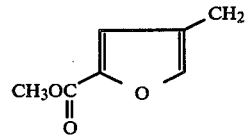 | $C_2H_5$ |
| 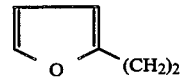 | n-$C_3H_7$ |
| 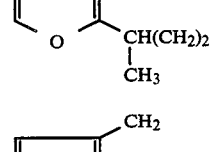 | H |
| 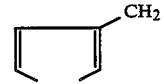 | H |

| $R^1$ | $R^2$ |
|---|---|
| 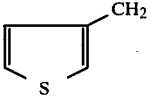 (thiophene-CH2) | CH3 |
| 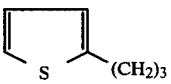 (thiophene-(CH2)3) | H |
| 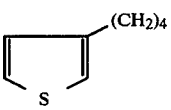 (thiophene-(CH2)4) | CH3 |
| —(CH2)4— | |
| —(CH2)2—O—(CH2)2— | |
| —(CH2)2—N(CH3)—(CH2)2— | |
| 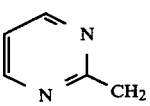 (pyrimidinyl-CH2) | H |
| 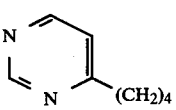 (pyrimidinyl-(CH2)4) | H |
| 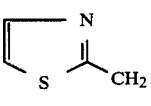 (thiazole-CH2) | H |
| 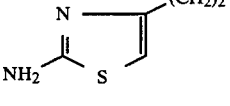 (aminothiazole-(CH2)2) | CH3 |
| 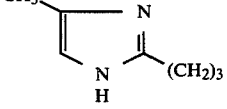 (methylimidazole-(CH2)3) | H |
| 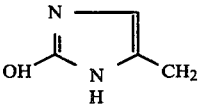 (hydroxyimidazole-CH2) | H |
| 2-pyridylmethyl | CH3 |
| 2,4-Cl2C6H3 | CH3 |
| 2-(COOCH2CH2CH3),5-ClC6H3 | H |
| 2-(HO),5-CH3C6H3 | H |
| 4,6-dimethylpyridin-2-yl-methyl | H |
| 3-CF3C6H4CH2CH2 | H |
| 4-n-C3H7C6H4(CH2)3 | H |
| 4-n-C3H7C6H4(CH2)3 | n-C3H7 |
| (CH3)2CHCH2 | H |
| CH3(CH2)5 | CH3 |
| CH3(CH2)4CH(CH3) | C2H5 |
| (CH3)2CH(CH2)5 | C2H5 |
| (CH3)2CH(CH2)6 | H |
| CH3(CH2)8 | CH3 |
| (CH3)CH(CH2)3 | CH3 |
| 2-CH3,4-FC6H3 | H |
| 2-FC6H4 | n-C4H9 |
| 4-FC6H4(CH2)3 | i-C4H9 |
| 2-Cl,4-CNC6H3 | CH3 |
| 3-CNC6H4CH2 | H |
| 4-(COOH)C6H4 | CH3 |
| 4-CH3O,2-(COOCH3)C6H3 | H |
| 3-(COOC2H5)C6H4CH2 | CH3 |
| 4-CNC6H4(CH2)4 | CH3 |
| 3-BrC6H4(CH2)2 | H |
| 2,4-(CH3)2C6H3(CH2)3 | H |
| 4-NO2C6H4CH2 | H |
| 4-(CH3COO)C6H4 | H |
| 2-(n-C3H7COO)C6H4 | CH3 |

| $R^1 + R^2 + N$ |
|---|
| pyrrolidino |
| piperidino |
| piperidino |
| morpholino |
| 4-methylpiperazino |

PREPARATION B

General methods for preparation of N-substituted guanylthioureas (IV).

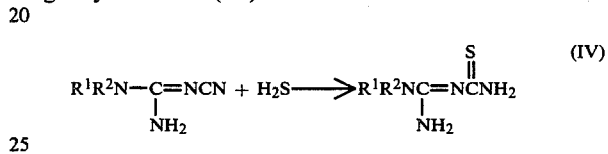

(i) 1-(n-Hexylguanyl)thiourea (IV, $R^1$=n-$C_6H_{13}$, $R^2$=H)

The procedure is a modification of that of Kurzer, *Org. Syn. Coll.* Vol. IV, p. 502 for the parent compound ($R^1$=$R^2$=H).

To a mixture of 4.5 g (0.027 mole) 1-n-hexyl-3-cyanoguanidine, 75 ml methanol and 0.5 ml diethylamine, hydrogen sulfide gas is introduced and bubbled through the mixture for eight hours. The mixture is stirred overnight at room temperature, then H2S passed through again for six hours and again stirred overnight. At this point thin-layer chromatography of the reaction mixture indicated the presence of starting material. The mixture was heated at reflux while bubbling H2S through for another six hours and reflux continued overnight. The solvent was evaporated in vacuo and the residue purified by flash silica gel chromatography eluting with 9:1 chloroform/methanol to afford 4.49 g product. Mass spectrum (m/e): 202 (M+).

(ii) Alternatively the compounds (IV) may be prepared by the method of Cutler and Shalit, U.S. Pat. No. 4,009,163 (Example 17) as illustrated below for 1-(benzylguanyl)thiourea.

To a solution of 6.73 g (38.6 mmole) 1-benzyl-3-cyanoguanidine in 100 ml methanol is added 2 ml diethylamine, the mixture cooled to 0° C. and saturated with hydrogen sulfide gas. The cold solution was transferred to a stainless steel bomb, sealed and the bomb heated at 80° C. for 48 hours. The mixture was then transferred to a flask, flushed with nitrogen to expel the excess hydrogen sulfide and the solvent evaporated in vacuo. The resulting residual oil was purified by flash chromatography (silica gel) eluting with 20:1 chloroform/methanol to obtain 3.06 g of product as a light yellow oil. Mass spectrum (m/e): 209 (M+).

(iii) The remaining 1-substituted-3-cyanoguanidines provided in Preparation A, Part (ii), are converted to N-substituted-guanylthioureas of formula (IV) by the above methods.

$$R^1R^2C=\overset{\overset{S}{\|}}{\underset{\underset{NH_2}{|}}{N}}CNH_2 \quad (IV)$$

| R¹ | R² | Mass Spectrum Molecular Ion (m/e) |
|---|---|---|
| n-Butyl | H | 174 |
| n-Pentyl | H | 188 |
| n-Heptyl | H | 216 |
| n-Octyl | H | 230 |
| n-Nonyl | H | 244 |
| 2-Heptyl | H | 216 |
| 2-Octyl | H | 230 |
| C₆H₅ | H | 194 |
| C₆H₅(CH₂)₂ | H | 222 |
| C₆H₅(CH₂)₃ | H | 236 |
| C₆H₅(CH₂)₄ | H | 250 |
| 4-ClC₆H₄CH₂ | H | 243 |
| 4-ClC₆H₄(CH₂)₂ | H | 256 |
| 4-ClC₆H₄(CH₂)₃ | H | 270 |
| 4-CH₃OC₆H₄CH₂ | H | 238 |
| 4-CH₃OC₆H₄(CH₂)₂ | H | 252 |
| 2-Thienylmethyl | H | 214 |
| n-Hexyl | CH₃ | 216 |
| —(CH₂)₅— | | — |

The remaining N-substituted-3-cyanoguanidines (V), provided in Preparation A, part (iii), are reacted with hydrogen sulfide by the above method to afford the corresponding N-substituted guanylthioures of formula $$R^1R^2N\underset{\underset{NH_2}{|}}{C}=\overset{\overset{S}{\|}}{N}CNH_2$$

where R¹ and R² are as defined for the starting compound (V).

PREPARATION C

2-Hydroxymethyl-4-bromoacetylimidazole hydrobromide (i) 3-Bromo-4-ethoxy-3-buten-2-one A mixture of 400 ml absolute ethanol and 60 ml toluene was heated to reflux and 20 ml of azeotrope was removed via a Dean Stark trap. To the ethanoltoluene solution was added 33.0 g (0.2 mole) of 3-bromo-4-hydroxy-3-buten-2-one and reflux was continued for 2 hours during which period three aliquots of 20 ml of ethanol-toluene were removed via the trap. The solution was concentrated in vacuo to give 38.6 g (100%) of 3-bromo-4-ethoxy-3-buten-2-one as a mobile oil. ¹H-NMR(DMSO-d₆)ppm(delta): 8.21 (s, 1H), 4.23 (q, 2H), 2.33 (s, 3H), 1.31 (s, 3H).

(ii) 2-Hydroxymethyl-4-acetylimidazole 9.7 g (0.05 mole) of 3-bromo-4-ethoxy-3-buten-2-one was combined with 5.53 (0.05 mole) of hydroxyacetamidine hydrochloride in 100 ml acetone to form a slurry. To the slurry at 25° C. was added 11.5 g (0.1 mole) of 1,1,3,3-tetramethylguanidine over a period of 5 minutes. After stirring for 48 hours the slurry was filtered and the mother liquors were concentrated in vacuo to an oil which was chromatographed on silica gel 60 (E. Merck) using chloroform as eluent to give 1.48 g (21%) of 2-hydroxymethyl-4-acetylimidazole, m.p. 147°–148° C. ¹H-NMR(DMSO-d₆)ppm(delta): 7.73 (s, 1H), 5.46 (very broad s, 1H), 4.5 (broad s, 2H), 2.4 (s, 3H).

(iii) 1.826 g (0.013 mole) of 2-hydroxymethyl-4-acetylimidazole was dissolved in 40 ml of 48% hydrobromic acid and 2.1 g (0.013 mole) of bromine was added. The reaction was warmed at 80° C. for 2 hours and then concentrated in vacuo to a solid. This material was triturated with isopropyl ether and the resultant solid was collected by filtration and was washed with ether and dried to give 2.2 g (56%) of 2-hydroxymethyl-4-bromoacetylimidazole hydrobromide, m.p. 183° C. with decomposition. ¹H-NMR(DMSO-d₆)ppm(delta): 8.8 (s, 1H), 4.8 (s, 2×2H).

PREPARATION D

4-Acetyl-2-methylimidazole (i) 1,2-Dichloro-1-buten-3-one $$\underset{\underset{Cl}{|}}{(CH_3COC}=CHCl)$$

A mixture of 392 g (5.0 mole) acetyl chloride and 1817 g (18.75 mole) cis,trans-1,2-dichloroethylene under anhydrous conditions is cooled to 0° C. (acetonedry ice bath). To this was added in portions 734 g (5.5 mole) anhydrous aluminum chloride while maintaining the mixture below 25° C., the aluminum chloride being rinsed in with an additional 606 g (6.25 mole) 1,2-dichloroethylene. After the addition is completed, the cooling bath is removed and the mixture is heated at reflux (50°–60° C.) overnight. The cooled reaction mixture is poured onto ice, the organic layer separated and the aqueous layer is extracted with 3×500 ml methylene chloride. The combined organic layers are stirred vigorously, 450 g sodium chloride added and the small amount of water which separates is removed. The organic layer is filtered through diatomaceous earth (Celite) to remove the inorganic salts, then added to a solution of 748 g (6 mole) sodium carbonate monohydrate in sufficient water to make 2.5 liters of solution. The resulting mixture is stirred for 1.5 hours, the precipitated solid removed by filtration and washed with methylene chloride. The organic layer is separated, the aqueous portion extracted with 2×200 ml methylene chloride and the combined organic layers are dried (Na₂SO₄). The solvent is removed by evaporation in vacuo and the residual oil distilled to afford 517.5 g (74.5%) of product as a pale yellow liquid, b.p. 40°–52° C. at 8 mm. ¹H-NMR(CDCl₃)ppm (delta): 2.50 (s, 3H), 7.55 (s, 1H).

(ii) 2-Chloro-1,1-dimethoxy-3-butanone $$\underset{\underset{Cl}{|}}{[CH_3COCHCH(OCH_3)_2]}$$

To a solution of 297 g (5.5 mole) sodium methoxide in 5 liters of methanol at 0° C. is added in a slow stream 695 g (5.0 mole) 1,2-dichloro-1-buten-3-one. After the addition is complete, the mixture is stirred at 0° C. for one hour, an additional 54 g (1.0 mole) sodium methoxide is added, and stirring continued at 0° C. for one hour. The mixture is allowed to stir at room temperature overnight, another g mole of sodium methoxide added and stirring continued for an hour. The mixture is filtered (filter aid) to remove salts, washing with fresh methanol. The filtrate is concentrated in vacuo to a slurry which is taken up in isopropyl ether and washed in turn with water, saturated sodium bicarbonate solution and brine, then dried over anhydrous magnesium sulfate. The extract is concentrated in vacuo to provide a residual oil which is distilled in vacuo to afford a main fraction of 628 g (75%) of product, b.p. 66°–75° C. at 8 mm. $^1$H-NMR(CDCl$_3$)ppm(delta): 2.33 (s, 3H), 3.43 (s, 3H), 3.47 (s, 3H), 4.23 (d, 1H), 4.63 (d, 1H).

(iiia) In 500 ml of dioxane are added 83.5 g (0.50 mole) 2-chloro-1,1-dimethoxy-3-butanone, 94.5 g (1.0 mole) acetamidine hydrochloride and 123 g (1.5 mole) sodium acetate and the mixture is heated at reflux overnight. The cooled reaction mixture is filtered through a silica gel pad on a sintered glass filter funnel, washing with 3500 ml of dioxane. The filtrate and washings are combined and evaporated in vacuo to provide a residual oil which is purified by chromatography on a silica gel column (600 g), eluting with ethyl acetate. Fractions of 200 ml each are collected. After 16 fractions the elution is with 95:5 ethyl acetate/methanol. Fractions 18–35 are combined and the solvent evaporated in vacuo to afford 28.82 g (46.4%) of the desired product. Recrystallization from 1:1 ethyl acetate/isopropyl ether yields 19.27 g (31%) of crystals, m.p. 132°–133° C. Another 4.24 g (6.8%) was obtained by reworking the mother liquor. $^1$H-NMR(CD$_3$OD)ppm(delta): 2.40 (s, 3H), 2.43 (s, 3H), 7.68 (s, 1H).

(iiib) A mixture of 1.66 g (10 mmole) 2-chloro-1,1-dimethoxy-3-butanone, 1.43 g (15 mmole) acetamidine hydrochloride and 2.05 g (25 mmole) sodium acetate in 50 ml dioxane is heated at reflux for 24 hours. The dioxane is evaporated in vacuo and the residual oil is flash chromatographed on silica gel (40:60 ethyl acetate/hexane, 40 mm) to obtain three fractions. The third fraction, a white solid (1.121 g) was rechromatographed (40 mm, acetone) to afford 933 mg (75.1%) of product as white solid which is pure as judged by its NMR spectrum in CDCl$_3$ and by TLC on silica gel (one spot, 1:9 methanol/chloroform).

PREPARATION E

By repeating the method of Preparation D, Part (iiia) or (iiib) but with the appropriate amidine hydrochloride of formula R$^4$C($=$NH)NH$_2$.HCl in place of acetamidine hydrochloride affords the following compounds in like manner.

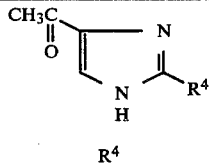

| R$^4$ |
|---|
| C$_2$H$_5$ |
| (CH$_3$)$_2$CH |
| CH$_3$(CH$_2$)$_2$ |
| CH$_3$(CH$_2$)$_3$ |
| CH$_3$(CH$_2$)$_4$ |
| CH$_3$(CH$_2$)$_5$ |
| (CH$_3$)$_2$CHCH$_2$ |
| (CH$_3$)$_2$CH(CH$_2$)$_3$ |
| HOCH$_2$ |

PREPARATION F

4-Acetyl-2-methylimidazole (i) 1-Benzyl-2-methylimidazole

To a slurry of 2.4 g (0.1 mole) of sodium hydride in 50 ml of dimethylformamide under a nitrogen atmosphere was added, with stirring, 8.2 g (0.1 mole) of 2-methylimidazole. A slow exothermic reaction occurred, the temperature reaching 43° C. When the exotherm subsided, the reaction was warmed on a steam bath to 70°–75° C. for a half-hour and then at 95° C. for 15 minutes to complete the reaction as evidenced by cessation of gas evolution. It was then cooled to 68° C. and 12.7 g (0.1 mole) of benzyl chloride added dropwise. An exothermic reaction occurred, the temperature reaching 95° C. After stirring for a half-hour following completion of addition, the reaction was poured into 600 ml of water and the product extracted with ethyl acetate (2×200 ml). The combined extracts were washed successively with water (1×400 ml), saturated aqueous sodium chloride solution (1×100 ml), then with 6N HCl (1×50 ml). The HCl wash was extracted with ether (1×25 ml) and then made basic by addition of sodium hydroxide. The yellow oil which separated was extracted into ether, the extract dried (MgSO$_4$) and evaporated under reduced pressure to give a pale yellow oil. Yield, 11.5 g (60.5%). NMR indicates the compound was obtained as the monohydrate. It was used as is in the hydroxymethylation reaction.

(ii) 1-Benzyl-4-hydroxymethyl-2-methylimidazole

A mixture of 8.5 g (0.05 mole) of 1-benzyl-2-methylimidazole monohydrate, 50 ml of 36% formaldehyde, 6 ml of acetic acid and 8.0 g (0.098 mole) of sodium acetate is stirred and heated at reflux for 26 hours. It was then stirred over a weekend (about 65 hours) at room temperature and neutralized with solid sodium carbonate. The neutral solution was extracted with ethyl acetate, the extract dried (MgSO$_4$) and evaporated under reduced pressure to an oil. Water (10 ml) and isopropanol (50 ml) were added to the oil, the solution stirred overnight then evaporated under reduced pressure. The oily residue obtained was taken up in water and the solution made strongly basic by addition of solid sodium hydroxide. It was chilled, layered with diethyl ether, and the white solid which formed removed by filtration and air dried. Yield=1.8 g (18%); m.p. 140°–146° C. It was purified by dissolution in 30 ml of hot (50° C.) ethyl acetate and filtration. Concentration of the filtrate to about two-thirds volume, and chilling, afforded 1.3 g of white solid; m.p. 147°–151° C. Thin layer chromatography in the system ethyl acetate:methanol:diethylamine (80:10:10) gave a single spot.

(iii) 1-Benzyl-2-methylimidazole-4-carboxaldehyde

A slurry of 9.0 g (0.446 mole) of 1-benzyl-4-hydroxymethyl-2-methylimidazole, 750 ml of methylene chloride and 50.0 g (0.575 mole) of manganese dioxide was stirred at room temperature for two hours. It was then filtered, the filter cake washed with methylene chloride and the combined filtrate and wash solutions evaporated under reduced pressure to give an oil. The oil was taken up in 100 ml of diethyl ether, 100 ml of hexane added and the solution seeded with a few crystals of the title compound. Concentration of the solution under a nitrogen sweep with periodic replacement of hexane afforded a crystalline product which was isolated by filtration: 7.2 g, 81% yield; m.p. 57°–60° C.

A second crop (0.75 g) was obtained by concentration of the filtrate; m.p. 57°–59.5° C. Total yield=89.4%.

(iv) 1-Benzyl-4-(1-hydroxyethyl)-2-methylimidazole

To a solution of 7.2 g (0.306 mole) of 1-benzyl-2-methylimidazol-4-carboxaldehyde in 100 ml of tetrahydrofuran was added 15 ml of 2.9M methyl magnesium chloride (0.044 mole) in tetrahydrofuran. A white precipitate formed immediately. The mixture was stirred at room temperature for 30 minutes and then heated with 50 ml of 25% aqueous ammonium chloride solution. The precipitate was filtered off, washed with tetrahydrofuran and air dried. The combined filtrate and wash solutions were dried ($Na_2SO_4$) and concentrated in vacuo to a solid residue. The residue was dissolved in 300 ml of boiling ethyl acetate, dried ($Na_2SO_4$) and concentrated to half volume under reduced pressure. The solid which separated upon cooling was filtered off and air dried. Total yield=7.1 g (90%); m.p. 162.5°–167.5° C.

(v) 4-(1-Hydroxyethyl)-2-methylimidazole

A Parr shaker was charged with 10.0 g (46.23 mmole) of 1-benzyl-4-(1-hydroxyethyl)-2-methylimidazole, 60 ml of methanol and 2.0 g of 5% palladium-on-carbon (50% water). Hydrogen gas was introduced to 30 psi (2.04 atmospheres), the mixture heated to 50° C. and shaken for 16 hours. It was cooled to 30° C., filtered through diatomaceous earth and the filter cake washed with 10 ml of methanol. Evaporation of the combined filtrate and wash under reduced pressure gave 6.44 g (97% yield) of the title product as an oil.

The product can be crystallized by adding enough tetrahydrofuran to dissolve the oil and stirring the solution at ambient temperature for two hours. The white crystalline solid was collected by filtration and air dried; m.p. 107°–111° C.

(vi) To a refluxing mixture of 1240 g (9.989 mole) of 4(5)-(1-hydroxyethyl)-2-methylimidazole in 10 liters of tetrahydrofuran was added 2200 g (25.293 mole) of manganese dioxide over a period of ten minutes. The mixture was refluxed overnight (18 hours), then filtered hot through diatomaceous earth. The filter cake was washed with 4 liters of tetrahydrofuran.

The combined filtrates and washings from two such reactions were stirred and concentrated at atmospheric pressure to about 6 liter volume at which point the mixture became solid. Ethyl acetate (2 liters) was added, the mixture heated to form a solution and to permit further removal of tetrahydrofuran. When the mixture became solid, an additional 2 liters of ethyl acetate was added and the heating repeated. When the mixture became solid, heating and stirring were discontinued and the mixture cooled overnight. Ethyl acetate (3.8 liters) was added and the solid mass broken up with the aid of a spatula. When it became stirrable, the slurry was heated at 50° C. for 3 hours, then cooled at 5° C. for one hour and filtered with suction. The yellow filter cake was washed with 1.5 liters of ethyl acetate at 5° C. then air dried. Yield=1887 g (76.08%); m.p. 128°–130° C.

PREPARATION G

4-Chloroacetyl-2-methylimidazole and its Hydrochloride Salt

Into a solution of 248 mg (2.0 mmole) 4-acetyl-2-methylimidazole in 20 ml methylene chloride was passed dry hydrogen chloride gas for five minutes, then 192 mg (6 mmole) dry methanol was added. To the resulting solution was added 297 mg (2.2 mmole) sulfuryl chloride and the mixture stirred for one hour at room temperature. Two additional portions of 155 mg each of sulfuryl chloride was then added at ten minute intervals to assure completion of the reaction. A few milliliters of methanol was added and the mixture was concentrated to dryness in vacuo. The resulting colorless oil was basified with solid sodium bicarbonate. The precipitated solid was collected, washed with water and dried under high vacuum to give 167 mg (53%) of fine white solid. $^1$H-NMR(DMSO-$d_6$)ppm(delta): 2.25 (s, 3H), 4.75 (s, 2H), 7.8 (s, 1H). Mass spectrum (m/e): 158 (M+), 109 (M-$CH_2Cl$).

When the above procedure was repeated on the same scale, but without methanol and subsequent additions of sulfuryl chloride, and stirring for two hours at room temperature, 395 mg (100%) of the hydrochloride salt was obtained, m.p. 159°–166° C., dec.

PREPARATION H

2-Aminomethylnapthalene

A mixture of 10.0 g (65.3 mmole) 2-cyanonaphthalene, 2.0 g Raney Nickel, 100 ml ethanol and 9 ml concentrated ammonium hydroxide was hydrogenated at 36 psi (2.53 kg/cm$^2$) for 4.5 days. The mixture was filtered and the filtrate concentrated in vacuo to an oil. The oil was distilled in vacuo to obtain the desired amine as a colorless liquid which solidified on standing. Yield 2.02 g. TLC on silica gel plates showed one spot at R$_f$ 0.1 upon development with 19:1 chloroform/methanol.

Hydrogenation of the appropriate nitrile of formula $(R^3)_2ArCN$, where $R^3$ and Ar are as defined above, by the same procedure affords the corresponding aminomethyl compound of formula $(R^3)_2ArCH_2NH_2$.

PREPARATION I

2-(3-Trifluoromethylphenyl)ethylamine

(i) 2-(3-trifluoromethylphenyl)acetonitrile

A mixture of 12.0 g (61.5 mmole) m-trifluoromethylbenzyl chloride, 9.56 g (195 mmole) sodium cyanide and 60 ml dimethylsulfoxide was heated at 50° to 80° C. for four hours and poured into water. The aqueous mixture was extracted with methylene chloride, the extracts dried over sodium sulfate and the solvent evaporated in vacuo to give 12.2 g of yellow oil which was used in the next step. $^1$H-NMR(CDCl$_3$)ppm(delta): 3.80 (s, 2H), 7.60 (s, 4H).

(ii) A mixture of 7.20 g (38.9 mmole) 2-(3-trifluoromethylphenyl)acetonitrile, 0.75 g Raney Nickel, 30 ml ethanol and 4.0 ml concentrated ammonium hydroxide was flushed with nitrogen, then hydrogenated at 3.5 kg/cm$^2$ for 18 hours. The catalyst was removed by filtration under nitrogen and the filtrate evaporated in vacuo to afford 6.86 g (93%) of the title amine as a red oil. $^1$H-NMR(CDCl$_3$)ppm(delta): 0.65–1.40 (bs, 2H), 2.65–3.40 (m, 4H), 7.30–7.60 (m, 4H).

By repeating the above procedures but starting with the appropriate starting chloromethyl or bromomethyl compound affords the corresponding amines, $(R^3)_2ArCH_2CH_2NH_2$, where $R^3$ and Ar are as defined above.

PREPARATION J

A general method for preparation of 3-arylpropylamines of the formula $(R^3)_2Ar(CH_2)_3NH_2$ is illustrated below.

3-(4-n-Propylphenyl)propylamine

(i) Ethyl 2-cyano-3-(4-n-propylphenyl)acrylate

A mixture of 20.0 g (90 mmole) 4-n-propylbenzaldehyde diethylacetal, 20.4 g (180 mmole) ethyl cyanoacetate, 7.2 g (93.4 mmole) ammonium acetate and 60 ml toluene are heated at reflux for six hours, cooled and poured into water. The resulting mixture was extracted with ethyl ether, dried (MgSO$_4$) and the volatiles evaporated in vacuo to afford 23.0 g crude yellow oil which was purified by chromatography on a silica gel column, eluting with 2:1 methylene chloride/hexane to give 20.58 g (94%) of the desired product. $^1$H-NMR(CDCl$_3$)ppm(delta): 0.85–1.95 (m, 8H), 2.45–2.70 (t, 2H), 4.15–4.60 (q, 2H), 7.15–8.05 (q, 4H), 8.25 (s, 1H).

(ii) 3-(4-n-Propylphenyl)propionitrile

A mixture of 20.50 g (84.3 mmole) of the product of Part (i), 8.75 g magnesium turnings and 200 ml methanol was stirred under a nitrogen atmosphere for six hours with periodic cooling to maintain a temperature of about 30° C. The mixture was acidified with hydrochloric acid, extracted with ethyl ether, the extracts washed with sodium bicarbonate solution, water, brine and dried over MgSO$_4$. Evaporation of solvent gave 23.8 g of crude product which was purified by column chromatography on silica gel, eluting with methylene chloride to provide 11.55 g (59%) of purified methyl 2-cyano-3-(4-n-propylphenyl)propionate. This was combined with 4.17 g sodium chloride, 175 ml dimethylsulfoxide and 5 ml water under nitrogen and the mixture heated at 150° C. for five hours. The reaction mixture was cooled, poured into 700 ml water and extracted with 2×500 ml ethyl acetate. The combined extracts were washed with brine (300 ml) dried over anhydrous sodium sulfate and concentrated in vacuo to give 12.5 g of the desired nitrile which was purified by distillation, b.p. 124°–128° C. (1.0 mm). $^1$H-NMR(CDCl$_3$)ppm(delta): 0.75–1.15 (t, 3H), 1.30–2.00 (m, 2H), 2.40–3.10 (m, 6H), 7.15 (s, 4H).

(iii) A mixture of 14.13 g (81.6 mmole) of the above nitrile (distilled), 1.5 g Raney Nickel, 60 ml ethanol and 8 ml concentrated ammonium hydroxide was hydrogenated at 3.5 kg/cm$^2$ for 18 hours. The mixture was flushed with nitrogen, the catalyst was removed by filtration and the filtrate concentrated in vacuo to give 12.3 g (84.8%) of clear oil. The oil was distilled to provide 8.60 g (59%) of pure amine as a colorless oil. $^1$H-NMR(CDCl$_3$)ppm(delta): 0.75–1.05 (t, 3H), 1.05 (s, 3H), 1.15–1.75 (m, 4H), 2.30–2.85 (m, 6H), 6.95–7.10 (m, 4H).

PREPARATION K

4-(4-Chlorophenyl)butylamine

A general method for preparation of 4-arylbutylamines of the formula (R$^3$)$_2$Ar(CH$_2$)$_4$NH$_2$ is illustrated below.

(i) 4-(4-Chlorophenyl)-3-butenoic acid

A mixture of 4-chlorobenzaldehyde (10.0 g, 68.2 mmole), 34.0 g (81.9 mmole) 3-(triphenylphosphonium)propionic acid bromide (prepared by reacting triphenylphosphine and 3-bromopropionic acid in xylene), 12.5 g sodium hydride (50% in mineral oil) and 200 ml dimethylsulfoxide were heated at 120° C. for five hours, cooled and poured into ice water. The mixture was made alkaline with sodium carbonate, extracted with ethyl ether and the extracts discarded. The aqueous phase was acidified, extracted again with ethyl ether, dried (MgSO$_4$) and the ether evaporated in vacuo to afford 6.9 g (51%) of the desired acid. $^1$H-NMR(CDCl$_3$)ppm(delta): 3.10–3.30 (d, 2H), 6.10–6.35 (m, 2H), 7.20 (s, 4H), 11.55–11.75 (bs, 1H).

(ii) 4-(4-Chlorophenyl)butanoic acid

A mixture of 19.5 g (98.2 mmole) of the unsaturated acid from Part (i), above, 1.95 g palladium-on-carbon catalyst and 200 ml ethyl acetate was hydrogenated at 3.5 kg/cm$^2$ and worked up in the usual manner to give the desired saturated acid in 91% yield. $^1$H-NMR(CDCl$_3$)ppm(delta): 1.75–2.80 (m, 6H), 6.95–7.40 (q, 4H), 9.15–10.25 (bs, 1H).

(iii) 4-(4-Chlorophenyl)butyric acid amide

A mixture of 8.8 g (44.3 mmole) of the saturated acid from Part (ii) and 45 ml thionyl chloride was heated at reflux for three hours. The mixture was cooled and excess thionyl chloride removed by evaporation in vacuo. The crude acid chloride was dissolved in 20 ml ethyl ether and the solution added dropwise to 67 ml concentrated ammonium hydroxide at 0° C. over 20 minutes. A tan solid formed immediately. The mixture was stirred one hour at 0° C., 80 ml water added and the mixture extracted with 3×100 ml ethyl ether. The combined ether layers were washed with brine, dried (MgSO$_4$) and concentrated in vacuo to give 8.70 g (97%) of amide. $^1$H-NMR(CDCl$_3$)ppm(delta): 1.60–2.40 (m, 4H), 2.45–2.85 (t, 2H), 5.25–6.10 (bs, 2H), 6.90–7.30 (q, 4H).

(iv) A mixture of 8.70 g (44 mmole) of amide from Part (iii), above, and 71 ml 1.0M boron hydride/tetrahydrofuran in 60 ml tetrahydrofuran was stirred four hours and the reaction quenched with 6N hydrochloric acid (36 ml). The mixture was extracted with ethyl ether, the extracts dried (Na$_2$SO$_4$) and concentrated in vacuo. The residual oil was stirred with isopropyl ether, filtered and the filtrate evaporated in vacuo to give 2.08 g. An additional 2.4 g was obtained by extraction of the liquors with ethyl acetate. $^1$H-NMR-(CDCl$_3$)ppm(delta): 1.15 (s, 2H), 1.30–1.90 (m, 4H), 2.40–2.90 (q, 4H), 6.90–7.35 (q, 4H).

I claim:

1. A compound of the formula

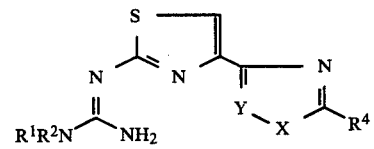

or a pharmaceutically acceptable acid addition salt thereof, wherein

X is NH and Y is CH or N, or

X is S and Y is CH;

R$^1$ is a straight or branched chain (C$_4$–C$_{10}$)alkyl, (R$^3$)$_2$C$_6$H$_3$ or (R$^3$)$_2$Ar(CH$_2$)$_n$ where n is an integer from 1 to 4, the R$^3$ groups are the same or different and are H, F, Cl, Br, I, CH$_3$, CH$_3$O, NO$_2$, NH$_2$, OH, CN, COOR$^5$, or OCOR$^5$ and R$^5$ is (C$_1$–C$_3$)alkyl; and Ar is the residue of a phenyl, naphthyl, furyl, thienyl, pyridyl, pyrimidinyl, thiazolyl, or imidazolyl group;

R$^2$ is H or (C$_1$–C$_4$)alkyl;

or when $R^1$ and $R^2$ are taken together with the nitrogen atom to which they are attached, they form pyrrolidino, piperidino, morpholino or 4-methylpiperazino; and $R^4$ is H, $(C_1-C_5)$alkyl, $NH_2$ or $CH_2OH$.

2. A compound according to claim 1 wherein X is NH.

3. A compound according to claim 2 of the formula

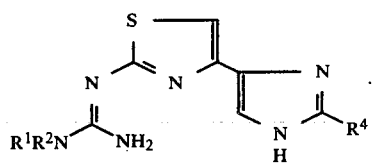

4. A compound according to claim 2 of the formula

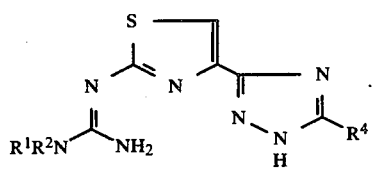

5. A compound according to claim 1 of the formula

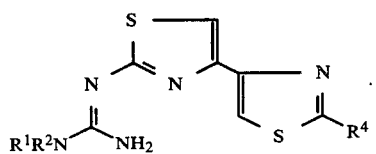

6. A compound according to claim 3 wherein $R^1$ is $(C_4-C_{10})$alkyl, $(R^3)_2C_6H_3$ or $(R^3)_2Ar(CH_2)_n$ where one $R^3$ is H and the other is H, $CH_3O$ or Cl, and Ar is the residue of a phenyl, furyl, thienyl, 3-pyridyl, 1-naphthyl or 2-naphthyl group.

7. A compound according to claim 6 wherein $R^2$ is H.

8. A compound according to claim 7 wherein $R^4$ is $(C_1-C_5)$alkyl.

9. A compound according to claim 8 wherein $R^4$ is $CH_3$.

10. A compound according to claim 9 wherein $R^1$ is n-pentyl, n-hexyl, n-heptyl, n-octyl, 2-octyl, phenyl, benzyl, phenylethyl, phenylpropyl, phenylbutyl, 4-chlorobenzyl, 4-chlorophenylethyl, 4-chlorophenylpropyl, 4-methoxybenzyl or 4-methoxyphenylethyl.

11. A compound according to claim 10 wherein $R^1$ is n-hexyl, 2-octyl or benzyl.

12. The compound according to claim 11: N-[4-(2-methylimidazol-4-yl)thiazol-2-yl]-N'-n-hexylguanidine or an acid addition salt thereof.

13. The compound according to claim 11: N-[4-(2-methylimidazol-4-yl)thiazol-2-yl]-N'-2-octylguanidine or an acid addition salt thereof.

14. The compound according to claim 11: N-[4-(2-methylimidazol-4-yl)thiazol-2-yl]-N'-benzylguanidine or an acid addition salt thereof.

15. A compound according to claim 9 wherein $R^1$ is furylmethyl, thienylmethyl, pyridylmethyl, 1-naphthylmethyl or 2-naphthylmethyl.

16. The compound according to claim 15: N-[4-(2-methylimidazol-4-yl)thiazol-2-yl]-N'-(2-furylmethyl)-guanidine.

17. The compound according to claim 15: N-[4-(2-methylimidazol-4-yl)thiazol-2-yl]-N'-(2-thienylmethyl)-guanidine.

18. A compound according to claim 4 wherein $R^1$ is $(C_4-C_{10})$alkyl, $(R^3)_2C_6H_3$ or $(R^3)_2Ar(CH_2)_n$ where Ar is the residue of a phenyl group.

19. A compound according to claim 18 wherein $R^2$ is H, and $R^4$ is H, $CH_3$ or $NH_2$.

20. A compound according to claim 19 wherein $R^1$ is n-hexyl, 2-octyl or benzyl.

21. The compound according to claim 20 wherein $R^1$ is n-hexyl, and $R^4$ is $CH_3$.

22. A compound according to claim 5 wherein $R^1$ is $(C_4-C_{10})$alkyl, $(R^3)_2C_6H_3$ or $(R^3)_2Ar(CH_2)_n$ where Ar is the residue of a phenyl group.

23. A compound according to claim 22 wherein $R^2$ is H, and $R^4$ is H, $CH_3$ or $NH_2$.

24. A compound according to claim 23 wherein $R^1$ is n-hexyl, 2-octyl or benzyl.

25. The compound according to claim 24 wherein $R^1$ is n-hexyl and $R^4$ is $CH_3$.

26. A pharmaceutical composition for inhibiting gastric ulcers in a mammal which comprises a pharmaceutically acceptable carrier and a gastric ulcer inhibiting amount of a compound according to claim 1.

27. A method of inhibiting gastric ulcers in a mammalian subject in need of such treatment which comprises administering to said subject a gastric ulcer inhibiting amount of a compound according to claim 1.

* * * * *